United States Patent [19]
Rosen

[11] Patent Number: 5,095,145
[45] Date of Patent: Mar. 10, 1992

[54] PREPARATION OF PURIFIED TEREPHTHALIC ACID FROM WASTE POLYETHYLENE TEREPHTHALATE

[75] Inventor: Bruce I. Rosen, Morton Grove, Ill.

[73] Assignee: Amoco Corporation, Chicago, Ill.

[21] Appl. No.: 609,202

[22] Filed: Nov. 5, 1990

[51] Int. Cl.$^5$ ............................................. C07C 51/487
[52] U.S. Cl. ................... 562/483; 562/486; 562/487
[58] Field of Search ..................... 562/483, 486, 487

[56] References Cited

U.S. PATENT DOCUMENTS

| | | | |
|---|---|---|---|
| 3,120,561 | 2/1964 | Chambret | 562/483 |
| 3,594,414 | 7/1971 | Katzschmann | 562/483 |
| 4,355,175 | 10/1982 | Pusztaszeri | 562/483 |
| 4,578,502 | 3/1986 | Cudmore | 560/79 |
| 4,578,510 | 3/1986 | Doerr | 562/483 |
| 4,605,762 | 8/1986 | Mandoki | 562/483 |
| 4,620,032 | 10/1986 | Doerr | 562/483 |
| 4,626,598 | 12/1986 | Packer et al. | 562/487 |

Primary Examiner—Jose G. Dees
Assistant Examiner—Vera C. Clarke
Attorney, Agent, or Firm—Gunar J. Blumberg; William H. Magidson; Ralph C. Medhurst

[57] ABSTRACT

A process is disclosed for producing fiber-grade terephthalic acid from waste polyethylene terephthalate film, fiber, bottles, manufacturing residues, and other manufactured articles. The process comprises depolymerizing waste polyethylene terephthalate in an aqueous mixture to obtain crude terephthalic acid having a b*-value less than 10.00 and an RFCVIS value of about 5000, or greater, which is thereupon hydrogenated in aqueous solution for a period of up to 8 hours. Organic and inorganic impurities are retained in the aqueous components. The purified terephthalic acid has a b*-value less than 2.00, a relative fluorescence concentration in visible light (RFCVIS) of less than 2500, metals content less than 100 ppmw and total organic impurities of less than 1000 ppmw.

6 Claims, No Drawings

PREPARATION OF PURIFIED TEREPHTHALIC ACID FROM WASTE POLYETHYLENE TEREPHTHALATE

FIELD OF THE INVENTION

The field of this invention relates to the preparation of purified terephthalic acid with optical and fluorescence properties suitable for preparation of polyethylene terephthalate from waste polyethylene terephthalate (PET). In one aspect, this invention relates to the preparation of purified terephthalic acid wherein color-producing compounds originating in the waste polyethylene terephthalate and color-producing compounds from the depolymerization of the waste polyethylene terephthalate are rendered colorless or water soluble and removed from crude terephthalic acid produced by the depolymerization process. The purified terephthalic acid produced from waste polyethylene terephthalate is a fiber-grade acid.

BACKGROUND OF THE INVENTION

The depolymerization of polyethylene terephthalate by hydrolysis at a high temperature and pressure in the absence of a base or acid, or a catalyst, is known in the art, see U.S. Pat. Nos. 4,578,502; 5,605,762; G.B. Patent 2,123,403; U.S. Pat. No. 4,578,510; Japanese Patent 56118420; Czech Patent 169,292; Japanese Patent 49076968; and Jap. Kokai JP 49/41329. However, the depolymerization of polyethylene terephthalate by neutral hydrolysis can result in the production of oligomeric byproducts (U.S. Pat. No. 4,578,510); derivatives of terephthalic acid (Wlokma Chem., 13(2), 144–55); cyclic trimers (JP 56118420). Additionally, the depolymerization product of waste polyethylene terephthalate in the form of bottles, film, fiber and other manufactured articles can contain dyes and other contaminants. For example, 100 parts of deep blue polyester fabric before hydrolysis contained 6.5% dyes and contaminants (JP 49020147). Accordingly, although various processes are available for hydrolyzing PET waste, the purification of the terephthalic acid typically requires several steps to remove dyes, pigments, and other impurities including inorganic compounds such as catalyst residues and organic compounds which can result from the depolymerization reaction.

U.S. Pat. No. 4,355,175, to Pusztaszeri, exemplifies the difficulties encountered in preparing a purified terephthalic acid from waste PET. Polyester scrap such as film (plain or silver-bearing), fabric, yarn, or bottles, was depolymerized at room temperature with a mixture of concentrated sulfuric acid and water to form crude terephthalic acid. Pusztaszeri teaches that an alkaline solution, which can be dark brown, or black in color, containing the crude terephthalic acid resulting from the depolymerization, is filtered to obtain a clear liquid which may be light brown in color (if dark colored, it must be reacted with activated charcoal and refiltered from the charcoal). The obtained solution is then acidified with sulfuric acid to precipitate the terephthalic acid (TPA). The TPA is then filtered and washed.

Regardless of the method of depolymerization and the method of purification of the resulting TPA, the variable nature of the impure crude terephthalic acid resulting from the depolymerization of waste polyethylene terephthalate from many sources and the variable nature of the impurities resulting therefrom and contained in the crude terephthalic acid, the process control, and thus quality assurance of the purified terephthalic acid, has been made difficult and costly. Because of this lack of quality assurance and its cost relative to that of virgin purified terephthalic acid, purified terephthalic acid from waste polyethylene terephthalate has not been considered as a viable economic replacement for fiber grade virgin purified terephthalic acid prepared from paraxylene.

It therefore is an object of this invention to provide a process to prepare fiber grade purified terephthalic acid from waste polyethylene terephthalate wherein metal content (ash content) is less than about 100 parts per million by weight (ppmw), total organic impurities are less than 1000 ppmw, $b^*$-value is less than 2 and relative fluorescence concentration in visible light (RFCVIS) is less than about 2500.

It is an object of this invention to provide an economical process for preparing fiber grade purified terephthalic acid from waste polyethylene terephthalate wherein origin of the waste terephthalate is from film (silver-bearing and non-silver bearing), fiber (including yarn and fabrics), bottles (clear or colored), and polyethylene terephthalate residues from manufacturing polyethylene terephthalate. Environmental problems relating to aspects of waste polyethylene terephthalate are reduced or eliminated.

Other objects of this invention will be obvious from the following discussion.

SUMMARY OF THE INVENTION

An economical process is disclosed for preparation of fiber grade purified terephthalic acid from waste polyethylene terephthalate wherein metal content of the purified terephthalic acid is less than 100 ppmw, organic impurities are less than 1000 ppmw, $b^*$-value is less than 2 and RFCVIS is less than about 2500. The waste polyethylene terephthalate can be from waste polyethylene terephthalate film, fiber, bottles, manufacturing residues from manufacturing polyethylene terephthalate and other manufactured articles. The waste polyethylene terephthalate is depolymerized to prepare a crude terephthalic acid with a $b^*$-value less than 15, preferably a $b^*$-value less than 10.00. Crude terephthalic acid of a $b^*$-value between 10.00 and 15.00 is recrystallized before hydrogenation to reduce its $b^*$-value to less than 10.00. The crude terephthalic acid is hydrogenated to a $b^*$-value of less than 2.00 and a RFCVIS value of less than about 2500. The color and fluorescence causing impurities resulting from the depolymerization are made water-soluble or colorless by the hydrogenation and are removed.

DETAILS OF THE INVENTION

In an embodiment of the process of this invention, polyester scrap is comminuted to suitable particle size by mechanical action, i.e., a crusher or grinding machine, slurried in water, and heated to a temperature within the range of from about 430° F. (221° C.) to about 600° F. (316° C.) for a period to hydrolyze the polyester scrap to crude terephthalic acid. The solution of crude terephthalic acid is cooled to precipitate the crude acid; the precipitate is separated by suitable means. The precipitate then is washed in water to remove water solubles present. The precipitate is reslurried in water and catalytically hydrogenated at a temperature within the range of from about 430° F. (221° C) to about 600° F. (316° C.). The hydrogenation reaction mixture is cooled to precipitate the terephthalic acid which then is separated from the mother liquid by suitable means, water washed and thereafter dried.

It is essential that the depolymerization reaction be limited to a period less than about 6 hours, preferably less than about 3 hours, more preferably less than 2 hours. Longer periods increase the presence of color-producing compounds.

It is essential for the preparation of fiber grade purified terephthalic acid that the precipitate of crude terephthalic from the hydrolysis step be water washed to remove water solubles, such as water-soluble inorganic compounds as well as water soluble organic compounds, from the precipitate before the precipitate is re-slurried in water and hydrogenated.

It is further essential that the water washed crude terephthalic acid from hydrolysis of the waste PET have a b*-value less than 10.00 before the crude terephthalic acid is hydrogenated. Crude terephthalic acid having a b*-value greater than 10.00 is unsuitable for hydrogenation to prepare purified terephthalic acid. Crude terephthalic acid having a b*-value greater than 10.00 upon hydrogenation can have a b*-value greater than the desired value of 2.00. Crude terephthalic acid having a b*-value equal to or greater than 10.00 and below about 15.00 can be recrystallized from water to reduce the b*-value below 10.00. Crude terephthalic acid having a b*-value greater than about 15.00 can be re-hydrolyzed and crystallized before further processing.

It is further essential that the crude terephthalic acid be hydrogenated for a period of up to about 8 hours. It has been found that the b*-value of purified terephthalic acid can be reduced by longer hydrogenation periods.

It is further essential that the precipitate from the hydrogenation mixture be water washed to remove water-soluble organic compounds produced by hydrogenating the previously water-insoluble organic compounds.

It is further essential that water be used as the solvent material instead of alcohols such as methanol or other solvents to eliminate the possibility of contamination of the purified terephthalic acid with solvent residue and to insure the removal of water-soluble impurities by water wash.

It is further essential that water by used as the solvent since a polycarboxylic acid is then produced in the hydrolysis step. If an alcohol, such as methanol is used, then a dialkyl phthalate is formed, for example, dimethyl terephthalate. Use of diols and polyols as a solvent would also result in the esterification reactions and require difficult separation steps.

It is further essential that water be used as the solvent to obtain a low-cost, economical process. Use of a solvent other than water would entail increased material costs and downstream equipment to recover the solvent, if such was considered necessary for cost or environmental reasons. Use of a solvent other than water would therefore make the process less economically desirable.

In preparation of the comminuted scrap polyethylene terephthalate, the polyethylene terephthalate scrap is subjected to the action of a granulator, or a crusher, or a grinding machine to reduce the scrap material to a suitable particle size which can be as large as about one-half inch, or about 2 cm, in length and about ⅛ inch, or 0.5 cm, thickness. The particles are slurried with water in a mole ratio of at least 2 moles of water to one mole of polyethylene terephthalate, preferably in a range of from about 3:1 to about 20:1 by weight of water to polyethylene terephthalate, preferably in a range of from about 3:1 to about 10:1, more preferably in a range of about 3:1 to reduce the amount of water required by the process.

The water-polyethylene terephthalate slurry is heated to hydrolysis temperature over a period of up to about 120 minutes to a temperature within the range of from about 430° F.(221° C.) to about 600° F.(312° C.), for a period of up to about 6 hours, preferably within the range of from about 500° F.(260° C.) to about 550° F.(288° C.), for a period of up to about 75 minutes, more preferably no more than 60 minutes, in the absence of any catalyst, acid, or base, at a pressure sufficient to maintain the slurry in liquid phase, suitably at a pressure within the range of from about 600 to about 1000 psig, preferably at a pressure within the range of from about 750 psig to about 850 psig.

The slurry of hydrolyzed polyethylene terephthalate is cooled to a temperature within the range of from about 275° F.(135° C.) to about 325° F. (163° C.), preferably about 300° F.(149° C.) to precipitate the crude terephthalic acid. The water-soluble inorganic compounds and water-soluble organic compounds present in the water slurry remain in solution. The precipitated crude terephthalic acid is separated from the slurry by suitable means, such as a filter or centrifuge. The water-soluble inorganic and organic impurities remain in the mother liquor and are thus separated from the crude terephthalic acid.

The crude terephthalic acid is thereupon water-washed to remove sorbed impurities from the particles of crude terephthalic acid and separated from the wash water by a suitable means such as a filter or centrifuge.

The b*-value of the separated crude terephthalic acid after the water wash it typically within the range of from about 15.00 to less than 10.00. If the b*-value is less than 10.00, the crude terephthalic acid is suitable for hydrogenation to reduce the b*-value to less than 2.00. If the b*-value is equal to or greater than 10.00 to about 15.00, further processing including reslurrying in water and recrystallization of the crude terephthalic acid, is required to reduce the b*-value to below 10.00 before hydrogenation. If the b*-value is greater than 15.00, the crude terephthalic acid can be re-processed by re-hydrolysis and recrystallization to reduce the b*-value below 10.00.

It is essential that the b*-value of the crude terephthalic acid before hydrogenation be less than 10.00. If b*-value of crude terephthalic acid is equal to or greater than 10.00, the b*-value is typically not reduced by hydrogenation to a level less than 2.00. Purified terephthalic acid having a b*-value greater than 2.00 is not preferred for polyethylene terephthalate polymer for film and fiber applications.

The washed crude terephthalic acid is thereupon re-slurried in water in a weight ratio of from about 3:1 to about 10:1, preferably about 4:1, water to crude terephthalic acid, to prepare an aqueous solution of at least 10 wt. % and hydrogenated, for a period of up to 8 hours, in the presence of a Group VIII metal catalyst at a temperature within the range of from about 430° F.(221° C.) to about 600° F.(316° C.) preferably from about 500° F.(260° C.) to about 550° F. (288° C.). Pressure is from about 950 psig to about 1200 psig. Preferable reaction time is from about 60 minutes to about 150 minutes. After hydrogenation, the reaction mixture is cooled to a range of from about 275° F. (135° C.) to about 325° F.(163° C.), preferably about 300° F.(149° C.) to precipitate the purified terephthalic acid. Upon filtration, the formerly water-insoluble impurities which have been hydrogenated to be water-soluble remain in the mother liquor and are separated from the purified terephthalic acid. A final water wash is used to remove any sorbed impurities on the particles of purified terephthalic acid. The washed purified terephthalic acid is thereupon dried at a temperature of from about 77° F.(25° C.) to about 212° F.(100° C.) to remove any remaining organic impurities by evaporation or sublimination.

As noted above, the crude terephthalic acid is recrystallized from water before hydrogenation to further reduce the b*-value is not less than 10.00.

The process embodying the present invention is conducted at an elevated temperature and pressure with the terephthalic acid to be hydrogenated dissolved in water.

Reactor and thus solution temperatures during hydrogenation can be in the range of about 430° F.(221° C.) to about 600° F.(312° C.), preferably about 530° F. to about 550° F., and more preferably about 535° F. to about 545° F.

Reactor pressure conditions primarily depend upon the temperature at which the hydrogenation process is carried out. Inasmuch as the temperature at which practical amounts of the impure terephthalic acid may be dissolved is substantially above the normal boiling point of the polar solvent, the process pressures are necessarily considerably above atmospheric pressure. The reactor pressure can be maintained by gaseous hydrogen alone or in admixture with an inert gas such as water vapor and/or nitrogen. The use of an inert gas in admixture with hydrogen also can provide an advantageous means for modulating the reactor hydrogen partial pressure, especially at relatively low hydrogen partial pressures. To this end, the inert gas is preferably admixed with hydrogen prior to introduction into the reactor. In generally, under normal operation, the reactor pressure during hydrogenation can be in the range of about 950 to about 1,200 pounds per square inch gauge (psig).

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case, the hydrogen partial pressure can be calculated from the known relative amounts of hydrogen and inert gas present in the admixture.

In yet another operating mode the reactor can be filled with the terephthalic acid solution so as to provide no reactor vapor space. That is, the reactor can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter is less than saturated with respect to hydrogen and the reactor itself is hydraulically full. Thus an adjustment of the hydrogen flow rate to the reactor will result in the desired proportional modulation of hydrogen concentration in the solution.

The amount of hydrogen supplied under reaction conditions usually is in the range of about 1 to about 5 moles over moles of crude terephthalic acid, and thus in excess over the stoichiometric amount required to reduce reducible impurities, such as dicarboxystilbene, as well as the characteristically yellow-colored impurities that may be present.

Hydrogenation of the impure terephthalic acid solution is effected in the presence of a Group VIII metal catalyst which can be used supported or unsupported. A wide variety of hydrogenation catalysts is available for this purpose. A typical Group VIII metal-bearing catalyst comprises about 0.01 to about 1 weight percent of a Group VIII metal, calculated as the elemental metal and based on the total weight of the catalyst, supported on a porous inert support structure such as charcoal. The support structure preferably has a surface area in the range of about 1,000 to about 2,000 square meters per gram. Group VIII metals particularly well-suited as catalysts for the present purposes are platinum and palladium. A particularly preferred catalyst is palladium on carbon.

Other catalysts effective for aqueous phase hydrogenation under the relatively mild hydrogenation conditions described hereinabove are listed in Kirk-Othmer, *Encyclopedia of Chemical Technology* (Wiley-Interscience), particularly in the chapters on Hydrogenation and Catalysts. See also U.S. Pat. Nos. 2,070,770 to Amend and No. 2,105,664 to Lazier. Illustrative other Group VIII metals suitable as catalysts for the present purposes are ruthenium, rhodium, osmium, and iridium.

The present purification process can be carried out in a batch mode as well as a continuous mode. For commercial scale purification of terephthalic acid the continuous mode is preferred. In any event, however, the b*-value and the relative fluorescence concentration in visible light (RFCVIS)) of the crude terephthalic acid and purified terephthalic acid are monitored so as to obtain the desired color level of the final product, a fiber-grade terephthalic acid.

An essential element of the process of the instant invention is that the purified terephthalic acid prepared by the invented process has a b*-value less than 2.

The color level of purified terephthalic acid as measured by the b*-value indicates the presence of various color bodies present in the material. The color level of the purified terephthalic acid has been found to relate directly to the procedure used to depolymerize the waste polyethylene terephthalate and the procedure used to hydrogenate the material.

The hydrogenation process is taught in U.S. Pat. No. 4,782,181, which is incorporated herewith by reference.

The color level of the purified product can be monitored or evaluated directly or indirectly, as described hereinbelow. The reactor hydrogen partial pressure can be adjusted to compensate for any detected impermissible deviation of the purified terephthalic acid from the desired color level. Adjustment can be made by the procedure taught in U.S. Pat. No. 4,782,181.

In one aspect, the color level of the purified product can be ascertained by measuring its b*-value on the Hunter Color Scale as described in Hunter, *The Measurement of Appearance*, Chapter 8, pp. 103-132, John Wiley & Sons, N.Y., N.Y. (1975), and in Wyszecki et al., *Color Science Concepts and Methods, Quantitative Data and Formulae*, 2d Ed., pp. 166-168, John Wiley & Sons, N.Y., N.Y. (1982).

More specifically, the b*-value of purified terephthalic acid can be determined using, for example, a Diano Match Scan Spectrophotometer as follows. Purified terephthalic acid is pressed into a pellet having a thickness of about 0.25 inch and diameter of about 1 inch. The pellet is then irradiated with white light that has been UV-filtered. The spectrum of the visible light reflected from the sample is determined and tristimulus values (X, Y, and Z) are computed using the CIE Standard Observer functions. Using the weighted-ordinate method, tristimulus values are obtained from the following equations:

$$X = \sum_{400}^{700} R\lambda x\lambda, \quad Y = \sum_{400}^{700} R\lambda y\lambda, \quad Z = \sum_{400}^{700} R\lambda z\lambda$$

where $R\lambda$ is the percent reflectance of the object at wavelength $\lambda$ and $x\lambda$, $y\lambda$ and $z\lambda$ are the Standard Observer functions at wavelength $\lambda$ for CIE Illuminate D65. The tristimulus values X, Y and Z, identify the color of the object in terms of the mixture of the primary lights that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100Y/Y_O)^{\frac{1}{3}} - 16$$

$$a^* = 500[(X/X_O)^{\frac{1}{3}} - (Y/Y_O)^{\frac{1}{3}}]$$

$$b^* = 200[(Y/Y_O)^{\frac{1}{3}} - (Z/Z_O)^{\frac{1}{3}}]$$

The L* value is a measure of the luminosity or whiteness of an object where L*=100 is pure white. L*=0 is black, and in-between is gray. The L* value is strictly a function of the tristimulus Y-value. The b*-value is a measure of the yellowness-blueness attribute where positive b*-values represent yellow appearance and negative b*-values represent blue appearance. The b*-value is a function of both tristimulus values Y and Z.

Alternatively, by the aforesaid indirect method, the color level, e.g., b*-value, of the purified product can be correlated with the optical density (OD) of the incoming feed utilized to adjust the reactor hydrogen partial pressure. Typically, the optical density values can be determined using a spectrophotometer and a light beam having a wavelength of 340 nanometers (nm) or millimicrons (mu), correlated with the product b*-value at a given hydrogen partial pressure for a specific catalyst, and then used to adjust the hydrogen partial pressure during a particular process run so as to produce a purified product having the desired b*-value.

It has been found that a 0.1 unit deviation in the b*-value of a product can be compensated by an adjustment in reactor hydrogen partial pressure of as low as about 5 psi to as high as about 60 psi, depending upon the activity of the catalyst employed. If a fresh, relatively high activity catalyst is utilized, the initial adjustment in hydrogen partial pressure for a 0.1 unit deviation in the b*-value usually is about 5 psi to about 7.5 psi. However, as the catalyst stabilizes, the adjustment in hydrogen partial pressure for a 0.1 unit deviation in the b*-value usually is about 40 psi to about 50 psi.

Similarly, it has been found that a 0.1 unit change in feed solution optical density at 340 nm($O_{340}$) causes about a 0.05-unit change in the b*-value of the purified terephthalic acid that is derived from that particular feed solution. Thus, a 0.1-unit change in $OD_{340}$ of the feed solution usually can be initially compensated by an adjustment in reactor hydrogen partial pressure of about 2.5 psi to about 4 psi for a fresh, relatively high activity catalyst. However, as the activity of catalyst stabilizes during use, a 0.1-unit change in $OD_{340}$ of the feed solution usually can be compensated by an adjustment in reactor hydrogen partial pressure of about 20 psi to about 25 psi.

The overall relationship among b*-value, hydrogen partial pressure, and optical density at 340 nm can also be expressed as $$b^*\text{-value} \propto A(H_2pp) + C(OC_{340})$$

wherein $H_2pp$ designates hydrogen partial pressure expressed in psi, $OD_{340}$ is the optical density value of the crude terephthalic acid feed solution. A has a value of about 0.001 to about 0.03, and C has a value of about 0.4 to about 1.4.

Similarly, the overall relationship among b*-value, solution hydrogen concentration, and optical density at 340 nm can be expressed as $$b^*\text{-value} \propto D(H_2\text{conc.}) + C(OD_{340})$$

wherein $H_2$conc. designates solution hydrogen concentration in cubic centimeters of hydrogen at 1 atmosphere absolute pressure and 0° C. (32° F.) dissolved per gram of crude terephthalic acid feed solution, $OD_{340}$ is the optical density value of the crude terephthalic acid feed solution, D has a value of about 0.2 to about 5.75, and C has a value of about 0.4 to about 1.4.

If it is desired to modulate the solution hydrogen concentration in a hydraulically full reactor directly by adjusting the flow of gaseous hydrogen to the hydrogenation reactor, then in such an event the hydrogen flow rate can be adjusted to provide a change in solution hydrogen concentration in the range of about 0.03 cc/g to about 0.3 cc/g for a 0.1 unit change in the product b*-value to be implemented, or in the range of about 0.015 cc/g to about 0.15 cc/g for an observed 0.1-unit change in $OD_{340}$ of the feed solution to the hydrogenation reactor.

The terephthalic acid concentration in the solution to be purified by hydrogenation can vary over a relatively wide range. The concentration can be as low as about 5 percent by weight or as high as about 35 percent by weight, based on the weight of the solution. Preferably, the solution concentration of terephthalic acid is in the range of about 10 to about 30 percent by weight.

An essential element of the process of the instant invention is that a purified terephthalic acid is prepared by the process which has a relative fluorescence concentration in visible light (RFCVIS) of less than about 2500.

The fluorescence characteristics of the purified product can be monitored by measuring the relative fluorescence concentration in visible light (RFCVIS) wherein the excitation is at a wavelength of 365 nanometers and the emission is at a wavelength greater than 407 nanometers, as measured by esterification liquid chromatography (ELC).

Furthermore, it has been found that the RFCVIS value correlates with the concentration of color producing fluorescent impurities in the crude terephthalic acid prepared from waste polyethylene terephthalate and the concentration of color producing fluorescent impurities in the purified terephthalic acid. Crude terephthalic acid from waste polyethylene terephthalate typically has been found to have a RFCVIS value of 5000, or greater.

In the process of depolymerization by hydrolysis of waste polyethylene terephthalate, additional impurities are generated in addition to the impurities already present in the waste polyethylene terephthalate. It has been found that many of these impurities fluoresce at wavelengths within the visible spectrum. Since the concentration of these impurities can affect the fluorescence attributes of the purified terephthalic acid, the reduction of the concentration of these impurities as measured by the fluorescence of the purified terephthalic acid is highly desirable to obtain fiber-grade terephthalic acid.

Although it is known that fluorescence of purified terephthalic acid derived from technical grade terephthalic acid can be decreased by passage of an aqueous solution of crude terephthalic acid through a liquid-filled layered particulate catalyst bed that contains plural layers of different hydrogenation catalysts, see U.S. Pat. No. 4,892,972, it has not been known that fluorescence could be reduced of crude terephthalic acid derived from hydrolysis of waste polyethylene terephthalate which contains fluorescent impurities in large amounts, i.e., from RFCVIS values of 5000, or greater to RFCVIS values of less than 2500. Hydrolysis of waste polyethylene terephthalate has been found to result in crude terephthalate acid with very high levels of fluorescence in the visible light spectrum because of the number of fluorescent compounds resulting from the depolymerization reaction and the high concentration of these compounds in the crude terephthalic acid.

Quite unexpectedly, it has been found that many of these fluorescent compounds can be hydrogenated to decrease the high level of fluorescence of these fluorescent compounds which result from hydrolysis of waste polyethylene terephthalate. Specifically, it has been found that high levels of fluorescent impurities present in crude terephthalic acid derived from waste polyethylene terephthalate can be decreased by the process of the instant invention to a level wherein the relative fluorescence concentration in visible light, as measured by esterification liquid chromatography, is less about 2500.

In summary, the instant invention comprises a process for producing fiber grade terephthalic acid having a b*-value less than 2.00, a relative fluorescence concentration in visible light of less than 2500, a metals content of less than 100 ppmw, and total organic impurities of less than 1000 ppmw, from waste polyethylene terephthalate film, fiber, bottles, manufacturing residues and other manufactured articles wherein the process comprises the following sequence of operations: (a) depolymerizing waste polyethylene terephthalate in an aqueous mixture of at least 2 moles of water per mole of said waste polyethylene terephthalate by heating said mixture to a temperature of from about 430° F.(221° C.) to about 600° F.(316° C.) at a pressure to maintain said aqueous mixture in liquid phase wherein said waste polyethylene terephthalate is depolymerized to produce an aqueous crude terephthalic acid solution; (b) cooling said solution to a temperature of from about 275° F.(135° C.) to about 325° F.(149° C.) from a precipitate of said crude terephthalic acid in said solution while retaining impurities in the aqueous component of said solution; (c) separating said precipitate of crude terephthalic acid from said solution and washing said precipitate of crude terephthalic acid with water at a temperature less than 275° F.(135° C.) to remove remaining water soluble impurities from the crude terephthalic acid to prepare a washed crude terephthalic acid having a b*-value less than 10.00, and a RFCVIS value of about 5000, or greater, washed crude terephthalic acid having a b*-value equal to or greater than 10.00 being re-cycled to the depolymerization reactor or to a crystallizer to recrystallize the crude terephthalic acid from solution to decrease the b*-value to less than 10:00; (d) reslurrying said precipitate of washed crude terephthalic acid having a b*-value less than 10.00 in water in a weight ratio of from about 3:1 to about 20:1, water to crude terephthalic acid, to prepare an aqueous solution of at least 5 wt. % of said washed crude terephthalic acid at a temperature of from about 430° F.(221° C.) to about 600° F.(316° C.) at a pressure sufficient to maintain said solution in liquid phase; (e) hydrogenating said solution at a temperature of from about 430° F.(221° C.) to about .600° F.(316° C.) in the presence of a Group VIII metal catalyst at a pressure of from about 950 psig to about 1200 psig wherein the amount of hydrogen supplied is in the range of from about 1 to 5 moles in excess over moles of crude terephthalic acid for a period of up to about 8 hours; (f) cooling said solution to a temperature of from about 275° F. (135° C.) to about 325° F.(149° C.) to form a precipitate of purified terephthalic acid while retaining impurities in the aqueous component of said solution; (g) separating said precipitate of purified terephthalic acid from said solution and washing said precipitate of purified terephthalic acid with water at a temperature less than about 275° F.(135° C.) to remove remaining water soluble impurities from the purified terephthalic acid; and (h) drying said purified terephthalic acid at a temperature of at least 77° F.(25° C.) wherein said purified terephthalic acid has a b*-value of less than 2.00, a relative fluorescence concentration in visible light of less than 2500, a metals content of less than 100 ppmw, and total organic impurities are less than 1000 ppmw.

In more detail, the said washed crude terephthalic acid having a b*-value equal to or greater than 10.00 recycled to a crystallizer is reslurried in water to prepare an aqueous solution at a temperature of from about 430° F. (221° C.) to about 600° F.(316° C.) at a pressure sufficient to maintain said aqueous solution in liquid phase, said solution is cooled to a temperature of from about 275° F.(135° C.) to about 325° F.(149° C.) to form a precipitate of said crude terephthalic acid having a b*-value less than 10.00 while retaining impurities in the aqueous portion of said solution, said precipitate of crude terephthalic acid being suitable for hydrogenation to prepare purified terephthalic acid.

In further detail, the said waste polyethylene terephthalate is depolymerized in an aqueous mixture of from about 3:1 to about 10:1 by weight of water to polyethylene terephthalate. The said Group VIII metal catalyst is supported or unsupported and selected from the group consisting of platinum, palladium, ruthemium, rhodium, osmium and iridium, preferably said catalyst is palladium on carbon. The said washed crude terephthalic acid can be present in a solution concentration in the range of from about 10 to about 30 wt. % in said hydrogenated solution.

The data in the following examples illustrate that purified terephthalic acid produced by the process of the instant invention with waste polyethylene terephthalate as the raw material has optical and fluorescence properties suitable for preparation of fiber or film grade polyethylene terephthalate. The data indicate the resulting polyethylene terephthalate using terephthalic acid derived from the waste material has properties equivalent to properties of polyethylene terephthalate prepared from virgin terephthalic acid commercially available.

The present invention is illustrated by the following Examples.

EXAMPLE I

A sample of polyethylene terephthalate 199.3 g, from waste beverage bottles was prepared. The particles were ¼ inch square and 10 mil thickness, which had been previously prepared by chopping in a laboratory blender with rotating knives. The sample was charged with 1204.5 g of distilled and deionized water to a 1 gal. titanium reactor complete with stirring means and thermocouple. The charged reactor was purged with nitrogen four times at a pressure of 400 psig. The reactor was closed and heated by external heating jacket over a period of 100 minutes to a temperature of 450° F. at a pressure sufficient to maintain the aqueous mixture substantially in liquid phase and held at that temperature for a period of 6 hours. The reaction mixture was allowed to cool to 25° C.(75° F.), at which time the reaction mixture was removed from the reactor and filtered. After drying, the dried powder weighted 151.0 g, representing a yield of 87.6 wt. % of theoretical.

EXAMPLE II

The procedure of Example I was repeated using 200.69 g of waste polyethylene terephthalate in 2000.7 g distilled and deionized water. Dried product weighed 160.7 g, a 92.6% yield of theoretical.

EXAMPLE III

The procedure of Example I was repeated with 405.0 g waste polyethylene terephthalate and 1212.0 g distilled and deionized water, with the exception that the hydrolysis temperature was 529° F. which was held for 1 hour. After filtration and wash with distilled and deionized water, the product was dried at room temperature. Product yield was 333.0 g, a 95.1% yield of theoretical.

EXAMPLE IV

A sample of 301 g of crude terephthalic acid in 1203 g of distilled and deionized water was charged to a titanium reactor. The crude terephthalic acid was prepared as in Example III. Catalyst was 4 g of palladium on carbon (0.5 wt. % Pd). After a purge with nitrogen, the reactor was heated to 537° F. Hydrogen, 100 lbs. and catalyst were added to the reactor for a period of 2 hours. At that time, the heat was removed and the reaction mixture allowed to cool to 300° F. at which temperature the mixture was filtered. After washing and drying at a temperature of 77° F.(25° C.), the product weighed 295 g, 98% of theoretical.

EXAMPLE V

The following example illustrates that depolymerization of polyethylene terephthalate results in the production of by-product impurities, some of which are color-producing compounds in the crude terephthalic acid resulting therefrom.

In the procedure of Example I, a sample of virgin PET, 50 gms, in the form of pellets, ⅛×⅛ inches was depolymerized. The virgin PET had been prepared from a purified terephthalic acid having a b*-value less than 2. The sample was charged to a one-gallon titanium reactor with 1001 grams of distilled and deionized water. The reactor was complete with stirring means, a thermocouple and external means for heating. After the charged reactor was purged with nitrogen four times at a pressure of 400 psig, the reactor was closed and heated over a period of 2 hours to a temperature of 500° F. and held at that temperature for a period of six hours. The reaction mixture was allowed to cool to room temperature to precipitate the crude terephthalic acid. Samples of the crude terephthalic acid, 40 grams, from Example I, and of the virgin PET, 40 grams, were then taken and analyzed by esterification liquid chromatography (ELC), inductively coupled plasma (ICP) and x-ray fluorescence (XRF). Results are in Table I. Comparative data for commercial terephthalic acid, TA-12, commercial purified terephthalic acid, PTA, and virgin polyethylene terephthalate, PET, are also listed in Table I.

TABLE I

|  | Commercial Terephthalic Acid (1) (range) | Crude Terephthalic Acid (2) | PTA (3) (range) | Virgin PET (4) |
|---|---|---|---|---|
| Organic Impurities (5) | | | | |
| Dicarboxybiphenyl, ppmw | 70-150 | 139 | 100-120 | 113 |
| Bis(carboxyphenyl)ethane, ppmw | 0 | 70 | 1-5 | 42 |
| Dicarboxystilbene, ppmw | 1-12 | 2 | 0 | 2 |
| RFCVIS | 0 | 5119 | 1127 | 2374 |
| Inorganic Impurities | | | | |

TABLE I-continued

|  | Commercial Terephthalic Acid (1) (range) | Crude Terephthalic Acid (2) | PTA (3) (range) | Virgin PET (4) |
|---|---|---|---|---|
| Cobalt, ppmw | 5-36 | 1 | >0.1 | 17 |
| Antimony, ppmw | 0 | 10 | 0 | 179 |
| Phosphorus, ppmw | 0 | N.D. | 0 | 24 |
| Ash, ppmw | 90-120 | >100 | 1-3 | >200 |

(1) Amoco TA-12, Amoco Chemicals Co., Chicago, IL
(2) Crude terephthalic acid from hydrolyzing waste polyethylene terephthalate
(3) Amoco PTA, Amoco Chemicals Co., Chicago, IL
(4) Polyethylene terephthalate prepared from virgin terephthalic acid and ethylene glycol, Goodyear Tire & Rubber Co., Akron, Ohio.
(5) Impurities causing loss of optical properties
N.D. Not detected The above data indicate typical levels of organic impurities in commercial and crude terephthalic acids which result in loss of optical properties. The data also indicate the high levels of compounds exhibiting fluorescence properties in crude terephthalic acid from waste polyethylene terephthalate.

EXAMPLE VI

The following example illustrates that depolymerization of polyethylene terephthalate results in the production of by-product impurities, some of which are color producing compounds in the crude terephthalic acid resulting therefrom and can be removed via hydrogenation.

In the procedure of Example I, a sample of waste PET from beverage bottles, 207 grams, in the form of squares, ¼×¼ inches, was depolymerized. The sample was charged to a one gallon titanium reactor with 2000 grams of distilled and deionized water. The reactor was complete with stirring means, a thermocouple and external means for heating. After the charged reactor was purged with nitrogen four times at a pressure of 400 psig, the reactor was closed and heated over a period of about 2 hours to a temperature of 525° F. and held at that temperature for a period of about 5 hours. The reaction mixture was allowed to cool to room temperature to precipitate the crude terephthalic acid. Samples of the crude terephthalic acid, 166 grams, and mother liquor were then taken and analyzed for b*-value, by inductively coupled plasma (ICP) or x-ray fluorescence (XRF).

In the procedure of Example IV, a sample of crude terephthalic acid, 300 grams, prepared as in the above procedure, in 1200 grams of distilled and deionized water was charged to the titanium reactor. Catalyst was added to the reactor, 4 grams, palladium on carbon (0.5 wt. % Pd). After a purge with nitrogen, the reactor was heated to 281° C.(537° F.). Hydrogen, 100 lbs, was added to the reactor for two hours. At that time, the heat was removed and the reaction mixture allowed to cool to 72° F., at which temperature the mixture was filtered. Samples, 294 grams, of hydrogenated terephthalic acid and mother liquor were taken and analyzed. Analysis was by b*-value, ICP or XRF. Results are in Table II.

TABLE II

Analysis of Depolymerized PET and Hydrogenated Terephthalic Acid

|  | Depolymerized | | Hydrogenated | |
|---|---|---|---|---|
|  | Crude TA ppm | Mother Liquor ppm | PTA ppm | Mother Liquor ppm |
| Zn | 0.1 | 0.5 | N.D. | 0.2 |
| Mn | 1.4 | 4.3 | 0.1 | 0.4 |
| Co | 2.0 | 6.4 | 0.1 | 0.4 |
| Na | 3.4 | 2.2 | 1.5 | 5.5 |
| K | 1.1 | N.D. | 0.3 | 1.4 |
| Ca | 1.5 | 2.1 | 1.2 | 4.0 |
| Sb | N.D. | 21.0 | N.D. | 0.6 |
| L* | 85.6 |  | 93.0 |  |
| a* | −0.28 |  | −0.91 |  |
| b* | 13.8 |  | 4.00 |  |

N.D. — Not detected

The above data indicate that the inorganic impurities of the depolymerization and hydrogenation procedure remain in the mother liquor to a large degree.

The data also indicate that, despite the hydrogenation as detailed above, the b*-value did not reduce below 2, which indicates that the b*-value of the starting material, the crude terephthalic acid, is critical in meeting the above specification. The crude terephthalic acid had a b*-value greater than 10.00. The result was that the hydrogenated product, the PTA, had a b*-value of 4.00, a b*-value above the required 2.00.

The above procedure was repeated, except that the hydrogenation period was increased to 6 hours, as follows: 290 g of crude terephthalic acid, 1160 g of distilled and deionized water, and 4 g of catalyst (0.5 wt. % Pd/C) were subjected to hydrogen, 100 psig, for 6 hours at 281° C.(530° F.). Color of the crude terephthalic acid was 7.15 as measured by b*-value. Color of the hydrogenated terephthalic acid was 0.88 as measured by b*-value.

EXAMPLE VII

In the procedure of Example I, a sample of clear polyethylene terephthalate, 200 g, from waste beverage bottles, in 2000 g of distilled and deionized water was depolymerized. The dried crude terephthalic acid weighed 161 g, yield 93 wt. % of theoretical. The L*, a* and b* values of the crude terephthalic acid were as follows:

| L* | 90.24 |
|---|---|
| a* | −0.48 |
| b* | 10.08 |

A sample of the dried crude terephthalic acid, 400 g, was reslurried in 2403 g of distilled and deionized water in a one-gallon titanium reactor. After a purge with nitrogen, the reactor mixture was heated to 537° F. to dissolve the crude terephthalic acid. The mixture was then allowed to cool to 200° F. to precipitate the product and filtered. The recrystallized product, 388 g, 97% of theoretical, was washed and dried at temperature of 77° F.(25° C.). The L*, a* and b* values of the recrystallized product were determined and were as follows:

| | |
|---|---|
| L* | 91.38 |
| a* | −0.44 |
| b* | 7.15 |

The recrystallization procedure was repeated but the mixture was filtered at 300° F. The L*, a* and b* values were as follows:

| | |
|---|---|
| L* | 88.11 |
| a* | −0.01 |
| b* | 7.30 |

The above data indicate that the b*-value of crude terephthalic acid from depolymerization of polyethylene terephthalate can be reduced by recrystallization but not enough to reduce the b*-value to below 2.00 if the b*-value of the crude terephthalic acid is greater than about 10.00.

EXAMPLE VIII

The recrystallized terephthalic acid, 290 g, from Example VII, of b*-value 7.15, was hydrogenated in the procedure of Example IV at a temperature of 533° F. for a period of 6 hours. After cooling to 300° F., the mixture was filtered. After washing and drying at a temperature of 77° F.(25° C.), the product weighed 277 g, 96% of theoretical. The product was analyzed. Details are in Table III.

TABLE III

| Analysis of Depolymerized PET and Hydrogenated Terephthalic Acid | | | |
|---|---|---|---|
| | Depolymerized | Hydrogenated | |
| | Crude TA ppm | PTA ppm | Mother Liquor ppm |
| Zn | 0.06 | 0.05 | 0.38 |
| Mn | 0.04 | 0.07 | 0.39 |
| Fe | 1.03 | 0.54 | 0.27 |
| Na | 1.11 | 1.10 | 4.50 |
| Mo | 0.36 | 0.26 | 0.15 |
| Ni | 0.23 | 0.16 | 0.21 |
| Al | 1.64 | 0.84 | 0.30 |
| Dicarboxystilbene | 7.9 | 0.0 | N.A. |
| L* | 91.38 | 94.02 | |
| a* | −0.44 | −0.17 | |
| b* | 7.15 | 0.88 | |
| RFCVIS | 9619 | 1127 | |

N.A. — Not analyzed

The above data indicate that most of the inorganic impurities remain in the mother liquor. The data also indicate that hydrogenation in the above detailed procedure reduces the b*-value to below 2.0.

The above data in Examples VII and VIII indicate that the b*-value of a crude terephthalic acid can be reduced from 10.00 or above to below 2.00 by recrystallization and hydrogenation. The data also indicate that a b*-value of crude terephthalic acid of less than 10.00 can be reduced to below 2.00 by hydrogenation of the crude terephthalic acid for a period of 6 hours.

EXAMPLE IX

In the procedure of Example I, pellets of green waste polyethylene terephthalate from waste green PET bottles were depolymerized. Heat up time was 130 minutes. Depolymerization temperature was 274° C.(525° F.). After 60 minutes of depolymerization a sample, 022-B, was taken. After a second 60 minutes, a second sample, 022-C, was taken. A third sample, 022-D, was taken after a third period of 175 minutes. Samples 022-B and 022-C were combined and analyzed for color by b*-value. Sample 022-D was also analyzed. Results are in Table IV.

TABLE IV

| Analysis of PET Depolymerized At 525° F. | | |
|---|---|---|
| | Composite Sample 120 Minutes | Sample 022-D 175 Minutes |
| L* | 91.54 | 68.18 |
| a* | −0.55 | 1.22 |
| b* | 5.22 | 15.88 |

The above data show the effect of increasing the depolymerization reaction period beyond 120 minutes upon the L*, a* and b* values.

EXAMPLE X

The procedure of Example VII was repeated with two samples of crude terephthalic acid obtained by depolymerizing clear polyethylene terephthalate from waste beverage bottles. The b* values were determined of the crude terephthalic acid. The crude terephthalic acid was then hydrogenated by the procedure of Example VIII. The b* values were determined. The results are in Table V.

TABLE V

| b* Values of Crude and Hydrogenated Terephthalic Acid | | |
|---|---|---|
| Sample No. | Crude TA b* | Hydrogenated TA b* |
| 12680-184 | 8.25 | 0.20 |
| 12680-186 | 8.25 | 0.50 |
| 12680-183 | 8.60 | 0.02 |

The above data indicate that b* values of less than 10.00 can be reduced by hydrogenation to a value less than 2.00.

EXAMPLE XI

Hydrogenated terephthalic acid, Sample No. 12680-184, 249 g, 12680-186, 212 g, and 12680-183, 292 g, were mixed to form Sample No. 12680-189-4, the properties of which were:

| | |
|---|---|
| L* | 94.18 |
| a* | −0.12 |
| b* | 0.39 |
| FI | 0.22 |
| O.D. | 0.09 |
| RFCVIS | 629 |

The above hydrogenated terephthalic acid was reacted with ethylene glycol in a molar ratio of 1.4 at a temperature of 544° F. in the presence of an esterification catalyst, 0.25 g antimony trioxide, to prepare polyethylene terephthalate. The properties of the polyethylene terephthalate prepared were measured. Properties of a polyethylene terephthalate sample prepared by reacting virgin terephthalic acid and ethylene glycol in a molar ratio of 1.4 were also measured. The virgin terephthalic acid was of commercial grade and had been prepared by oxidizing paraxylene and subsequent purification by conventional procedures to produce purified terephthalic acid with a b*-value of 1.02.

Properties of the polyethylene terephthalate of the two polymers were as follows.

TABLE VI

| PTA Source | Comparison of PET Properties | | | | |
|---|---|---|---|---|---|
| | L* | a* | b* | IV (1) | CEG (2) |
| Commercial Grade | 87.56 | −0.94 | 2.40 | 0.631 | 16.8 |
| Waste Polyethylene Terephthalate | 84.54 | −0.56 | 3.85 | 0.630 | 16.8 |

(1) IV — Inherent viscosity
(2) CEG — Carboxyl end groups

The above data indicate that polyethylene terephthalate prepared with purified terephthalic acid from waste polyethylene terephthalate by depolymerization and hydrogenation as in Example IX has properties equivalent to properties of polyethylene prepared from virgin terephthalic acid commercially available.

EXAMPLE XII

The following example illustrates that hydrogenation of up to about 6 hours can be required to reduce b* values greater than 2.00 but less than 10.00 to less than 2.00.

In the procedure of Example VI, a sample of waste green PET from beverage bottles, 405 grams, in the form of squares, ¼ × ¼ inches, was depolymerized. Samples of the crude terephthalic acid, 10 grams, were taken and analyzed for b*-value. Samples of the crude terephthalic acid, 300 grams, in 1200 gram water, were then taken and hydrogenated by the procedure of Example IV for a period of 4 hours at 537° F. Catalyst was 4 g of palladium in carbon (0.5 wt. % Pd). The b*value of the hydrogenated terephthalic acid was determined to be only slightly decreased. The hydrogenation procedure was repeated with 145 grams terephthalic acid in 1200 grams distilled and deionized water, 4 grams Pd catalyst at 537° F. Period of hydrogenation was 5 hours. Details are in Table VII.

TABLE VIII

| Hydrogenation of Crude Terephthalic Acid From Waste Green Polyethylene Terephthalate | | | |
|---|---|---|---|
| Sample | L* | a* | b* |
| No. 14633-029 (Crude TA) | 91.43 | −1.29 | 4.07 |
| No. 14633-056 (Hydrogenated TA From No. 14633-029) | 90.54 | −0.90 | 3.02 |
| No. 14633-063 (Hydrogenated TA From No. 14633-056) | 95.10 | −0.08 | 0.44 |

The above data indicate that a lengthened hydrogenation residence time is effective in decreasing b*-value to below 2.00. The second procedure, Sample No. 14633-063, utilized what was effectively a longer residence time. A smaller sample, No. 14633-063, 145 grams, was hydrogenated for a longer period, five hours, than the larger sample, No. 14633-056, 300 grams, which was hydrogenated for a period of four hours. The combined elements of smaller sample size and longer hydrogenation period effectively increased residence time for the smaller sample versus the residence time of the larger sample which was hydrogenated for a shorter period.

That which is claimed is:

1. A process for producing fiber grade terephthalic acid having a b*-value less than 2.00, a relative fluorescence concentration in visible light of less than 2500, a metals content of less than 100 ppmw, and total organic impurities of less than 1000 ppmw, from waste polyethylene terephthalate film, fiber, bottles, manufacturing residues and other manufactured articles wherein the process comprises the following sequence of operations:

(a) depolymerizing waste polyethylene terephthalate in an aqueous mixture of at least 2 moles of water per mole of said waste polyethylene terephthalate by heating said mixture to a temperature of from about 430° F. to about 600° F. at a pressure to maintain said aqueous mixture in liquid phase wherein said waste polyethylene terephthalate is depolymerized to produce an aqueous crude terephthalic acid solution;

(b) cooling said solution to a temperature of from about 275° F. to about 325° F. to form a precipitate of said crude terephthalic acid in said solution while retaining impurities in the aqueous component of said solution;

(c) separating said precipitate of crude terephthalic acid from said solution and washing said precipitate of crude terephthalic acid with water at a temperature less than 275° F. to remove remaining water soluble impurities from the crude terephthalic acid to prepare a washed crude terephthalic acid having a b*-value less than 10.00, and a RFCVIS value of about 5000, or greater, washed crude terephthalic acid having a b*-value equal to greater than 10.00 being re-cycled to the depolymerization reactor or to a crystallizer to recrystallizer the crude terephthalic acid from solution to decrease the b*-value to less than 10:00;

(d) reslurrying said precipitate of washed crude terephthalic acid having a b*-value less than 10.00 in water in a weight ratio of from about 3:1 to about 20:1, water to crude terephthalic acid, to prepare an aqueous solution of at least 5 wt. % of said washed crude terephthalic acid at a temperature of from about 430° F. to about 600° F. at a pressure sufficient to maintain said solution in liquid phase;

(e) hydrogenating said solution at a temperature of from about 430° F. to about 600° F. in the presence of a Group VIII metal catalyst at a pressure of from about 950 psig to about 1200 psig wherein the amount of hydrogen supplied is in the range of from about 1 to 5 moles in excess over moles of crude terephthalic acid for a period of up to about 8 hours;

(f) cooling said solution to a temperature of from about 275° F. to about 325° F. to form a precipitate of purified terephthalic acid while retaining impurities in the aqueous component of said solution;

(g) separating said precipitate of purified terephthalic acid from said solution and washing said precipitate of purified terephthalic acid with water at a temperature less than about 275° F. to remove remaining water soluble impurities from the purified terephthalic acid; and (h) drying said purified terephthalic acid at a temperature of at least 77° F. wherein said purified terephthalic acid has a b*-value of less than 2.00, a relative fluorescence concentration in visible light of less than 2500, a metals content of less than 100 ppmw, and total organic impurities are less than 1000 ppmw.

2. The process of claim 1 wherein said washed crude terephthalic acid having a b*-value equal to or greater than 10.00 recycled to a crystallizer is reslurried in water to prepare an aqueous solution at a temperature of from about 430° F. to about 600° F. at a pressure sufficient to maintain said aqueous solution in liquid phase, said solution is cooled to a temperature of from about 275° F. to about 325° F. to form a precipitate of said crude terephthalic acid having a b*-value less than 10.00 while retaining impurities in the aqueous portion of said solution, said precipitate of crude terephthalic acid being suitable for hydrogenation to prepare purified terephthalic acid.

3. The process of claim 1, wherein said waste polyethylene terephthalate is depolymerized in an aqueous mixture of from about 3:1 to about 10:1 by weight of water to polyethylene terephthalate.

4. The process of claim 1 wherein said Group VIII metal catalyst is supported or unsupported and selected from the group consisting of platinum, palladium, ruthemium, rhodium, osmium and iridium.

5. The process of claim 1 wherein said catalyst is palladium on carbon.

6. The process of claim 1 wherein said washed crude terephthalic acid is present in a solution concentration in the range of from about 10 to about 30 wt. % in said hydrogenated solution.

* * * * *

UNITED STATES PATENT AND TRADEMARK OFFICE
CERTIFICATE OF CORRECTION

PATENT NO. : 5,095,145
DATED : March 10, 1992
INVENTOR(S) : Bruce I. Rosen

It is certified that error appears in the above-indentified patent and that said Letters Patent is hereby corrected as shown below:

| Col. | Line | |
|---|---|---|
| 1 | 26 | "U.S. Pat. Nos. 4,578,502; 5,605,762;" should read --U.S. Pat. Nos. 4,578,502; 4,605,762-- |
| 1 | 40 | "(JP 49020147)" should read --(JP 49020146)-- |
| 8 | 35 | "$b^*$-value $\propto$ A($H_{2pp}$)+C($OC_{340}$)" should read --$b^*$-value $\propto$ A($H_{2pp}$)+C($OD_{340}$)-- |
| 16 | 31 | "The procedure of Example VII" should read --The procedure of Example VIII-- |
| 18 | 43-44 | "recrystallizer" should read --recrystallize-- |

Signed and Sealed this

Fifth Day of October, 1993

Attest:

BRUCE LEHMAN

Attesting Officer

Commissioner of Patents and Trademarks